(12) United States Patent
Mitterer et al.

(10) Patent No.: US 7,659,380 B2
(45) Date of Patent: Feb. 9, 2010

(54) METHOD OF ISOLATION AND PURIFICATION OF TRYPSIN FROM PRONASE PROTEASE AND USE THEREOF

(75) Inventors: Artur Mitterer, Orth/Donau (AT); Christa Tauer, Vienna (AT); Manfred Reiter, Vienna (AT); Wolfgang Mundt, Vienna (AT)

(73) Assignee: Baxter Healthcare S.A., Glattpark (Opfikon) (CH)

( * ) Notice: Subject to any disclaimer, the term of this patent is extended or adjusted under 35 U.S.C. 154(b) by 0 days.

(21) Appl. No.: 11/788,714

(22) Filed: Apr. 20, 2007

(65) Prior Publication Data

US 2007/0249015 A1    Oct. 25, 2007

Related U.S. Application Data

(62) Division of application No. 10/944,218, filed on Sep. 17, 2004, now Pat. No. 7,223,595, which is a division of application No. 10/006,223, filed on Dec. 10, 2001, now Pat. No. 6,830,917.

(51) Int. Cl.
| | |
|---|---|
| *C07K 1/00* | (2006.01) |
| *C07K 1/14* | (2006.01) |
| *C07K 1/22* | (2006.01) |
| *C07K 14/195* | (2006.01) |
| *C12N 9/76* | (2006.01) |

(52) U.S. Cl. .................. 530/415; 530/350; 530/412; 435/183; 435/213

(58) Field of Classification Search ................. None
See application file for complete search history.

(56) References Cited

U.S. PATENT DOCUMENTS 4,973,554 A * 11/1990 Luong et al. ............... 435/213

OTHER PUBLICATIONS

Ellquali et al., Affinity of trypsin for Amidine Derivatives Immobilized on Dextran-Coated Silica Supports, Chromsymp, 2215, p. 255-265 (1991).*
Hatanaka et al., "Interactions of derivatives of guanidinophenylalanine and guanidinophenylglycine with Streptomyces griseus trypsin," Biochemica et Biophysica Acta, vol. 832, pp. 274-279 (1985).*
Koo et al., "Purification and characterization of Streptomyces griseusStreptomyces griseus trypsin overexpressed in Streptomyces lividans, " Journal of Microbiology and Biotechnology, vol. 8(4), pp. 333-340 (1998).*
Shimura et al., Affinophoresis of Trypsins, Journal of Biochem, vol. 92, p. 1615-1622 (1982).*

* cited by examiner

*Primary Examiner*—Zachariah Lucas
(74) *Attorney, Agent, or Firm*—Townsend and Townsend and Crew LLP

(57) ABSTRACT

The present invention provides methods of isolation and purification of *Streptomyces griseus* trypsin (SGT) from PRONASE protease mixture in a single affinity chromatography step and uses of the purified SGT.

7 Claims, 4 Drawing Sheets

METHOD OF ISOLATION AND PURIFICATION OF TRYPSIN FROM PRONASE PROTEASE AND USE THEREOF

CROSS-REFERENCES TO RELATED APPLICATIONS

This application is a division of U.S. Ser. No. 10/944,218, filed Sep. 17, 2004, now U.S. Pat. No. 7,223,595, issued on May 29, 2007, which is a divisional of application Ser. No. 10/006,223, filed Dec. 10, 2001, now U.S. Pat. No. 6,830,917, issued Dec. 14, 2004, each of which is hereby incorporated by reference in its entirety.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

FIELD OF THE INVENTION

The present invention is directed to methods of isolation and purification of *Streptomyces griseus* trypsin (SGT) from PRONASE protease mixture in a single affinity chromatography step and uses of the purified SGT.

BACKGROUND OF THE INVENTION

Trypsin is a serine protease present in the digestive tract of a wide variety of mammals. Its function is the hydrolytic cleavage of peptide bonds, thus reducing the size of large proteins and making them accessible to further degradation by other proteases. Trypsin is used in biotechnological applications, especially in the cultivation of mammalian cells, where it serves as tool for the disintegration of large cell aggregates, or for the removal of cells from surfaces like microcarriers or cultivation trays. Trypsin is also used as a protein degrading enzyme in the processing of non-trypsin sensitive biopolymers. Because of its well known specificity, trypsin is also used as a selective protein cleavage tool in both analytical and preparative processes. Trypsin can be inactivated or inhibited by a number of specific or non-specific protease inhibitors, many of them belonging to the serpine family. The most widely used in biotechnological applications is a trypsin inhibitor from soy beans. As most of these trypsin inhibitors are very specific, they are inactive against other contaminating proteases.

Trypsin is typically prepared from the duodenal glands of various animal species and purified to different grades of purity. The purification of trypsin can be performed by a number of different biochemical processes, including precipitation, ion exchange chromatography and affinity chromatography. It has been shown that prepurified bovine trypsin (Type I) binds to benzamidine immobilized on an insoluble carrier and can be eluted by high concentrations of guanidine or arginine or by decreasing the pH of the eluant (Ellouali et al. (1991) *Chromsymp.* 2215:255-265). The mammalian pancreas from which trypsin is derived also contains the serine protease chymotrypsin, which is very similar to trypsin in its physiochemical properties, including the interaction with and affinity to amidine derivatives. As a result, these two proteins are difficult to separate. Depending on the purification method, purified trypsin preparations therefore may contain varying amounts of contaminating enzymes, particularly-chymotrypsin. Furthermore, mammalian-derived trypsin may contain adventitious agents, such as viruses and prions. Since the discovery of the action of TSE agents, and the possibility of their transmission to humans, there is an ongoing discussion about the use of human or animal derived materials in biotechnology processes providing pharmaceuticals for human use.

PRONASE protease mixture from the microbial organism *Streptomyces griseus* (S.g.), is a commercially available alternative to trypsin prepared from animal tissues. PRONASE protease mixture has been used for the preparation of primary cell cultures from tissues and for the detachment of cells from surfaces, microcarrier cell cultures and growth of VERO cells in suspension in serum-free media (Weinstein (1966) *Exper. Cell Res.* 43:234-236; Manousos et al. (1980) *In vitro* 16:507-515, Litwin (1992) *Cytotechn.* 10:169-174). The exact mechanism of its action is not known. PRONASE protease mixture is known to be a mixture of different enzymes, including various types of endopeptidases, (serine and metalloproteases), exopeptidases (carboxypeptidase and aminopeptidase), neutral protease, chymotrypsin, trypsin, carboxypeptidase, aminopeptidase, and neutral and alkaline phosphatase.

After enzyme treatment, the activity of trypsin is usually neutralized by the addition of fetal calf serum, which contains a number of specific and non-specific protease inhibitors. However, media free of serum and protein (particularly from mammalian sources) are preferred in cell culture media used for production of vaccine and therapeutic proteins. Therefore, use of serum-free media, which are devoid of any trypsin inhibitor activity, makes it necessary to identify new sources of inhibitor activity. Because PRONASE protease mixture is a mixture of a variety of proteases, inhibition of protease activity requires a mixture of different inhibitors, leading to a very complex and expensive process. The protein load arising from use of PRONASE protease mixture and the composition of inhibitors in a serum-free culture therefore would be much higher compared to a culture using mammalian-derived trypsin and specific trypsin-inhibitor. Furthermore, the addition of PRONASE protease mixture to the culture medium would also adversely effect the purification process, because more protein is present in the medium.

The trypsin-like activity of PRONASE protease mixture, commonly known as *Streptomyces griseus* trypsin (SGT) shows a sequence identity of approximately 33% to bovine trypsin (Olafson et al. (1975) *Biochem* 14:1168-1177). *Streptomyces griseus* trypsin has been purified by chromatographic techniques using different types of ion exchange resins. These methods typically use stable matrices, which minimize the problem of bleeding of the ligand into the product during elution. These methods, however, have relatively low selectivity, leading to purification factors in the range of <10. As a result, to achieve a high degree of purity, several steps have to be combined, which in turn may cause autodigestion of the trypsin and therefore loss of activity. Purification by ion-exchange chromatography on CM-Sephadex, with further purification performed by rechromatography on an ion exchange column has been described by Jurasek et al. (1971) *Can. J. Biochem.* 49:1195-1201; and Olafson et al. (1975a) *Biochem.* 14:1168-1.177; and (1975b) *Biochem.* 14: 1161-1167. Miyata et al. (1991) *Cell Structure and Function* 16:39-43, describes a three step cation exchange chromatography process to purify SGT. SGT is found to migrate as a single band in PAGE with a molecular weight of about 30,000 and having an esterase activity higher than bovine trypsin as determined by BAEE assay. However, even SGT purified by three step chromatography purification methods was found to be slightly contaminated by carboxypeptidase B-like activity.

SGT has also been purified from PRONASE protease mixture by affinity chromatography using oligopeptides derived from tryptic digest of salmine as highly specific ligand for SGT. Elution of the trypsin-like activity from the mixture of protease in PRONASE protease mixture with HCl revealed purified SGT which was, however, found to be contaminated by carboxypeptidase B-like activity (Kasei et al. (1975) *J. Biochem.* 78:653-662; Yokosawa et al. (1976) *J. Biochem.* 79:757-763). For analytical purposes only, SGT was also separated from PRONASE protease mixture by affinophoresis using benzamidine as a ligand (Shimura et al. (1982) *J. Biochem.* 92:1615-1622).

There exists a need for a simple large-scale method for isolation and separation of the active trypsin-like fraction of PRONASE protease mixture. This would allow a controlled system for use in cell culture methods and provide a defined activity of the fraction from a microbial source, which would not bear the risk of contaminants of human pathogens.

There also exists a need to avoid contaminants derived from cell culture medium additives during cell propagation/growth, biomass production and product production process. Reduction of the protein load in a cell culture medium would allow production of highly pure protein products using conventional purification methods.

BRIEF SUMMARY OF THE INVENTION

It is therefore an object of the present invention to provide for a method for isolation of purified *Streptomyces griseus* trypsin (SGT) from PRONASE protease mixture.

It is also an object of the invention to provide for a preparation of purified SGT having high specific activity.

It is another object of the invention to provide for use of purified SGT in biotechnology processes.

It is another object of the invention to provide for use of using purified SGT for production of a biomass of eukaryotic cells.

It is another object of the invention to provide for use of purified SGT for production of virus or virus antigen.

It is also an object of the invention to provide for use of purified SGT for production of biological products with cells passaged and subcultured with purified SGT only.

DETAILED DESCRIPTION OF THE INVENTION

Figure 1:
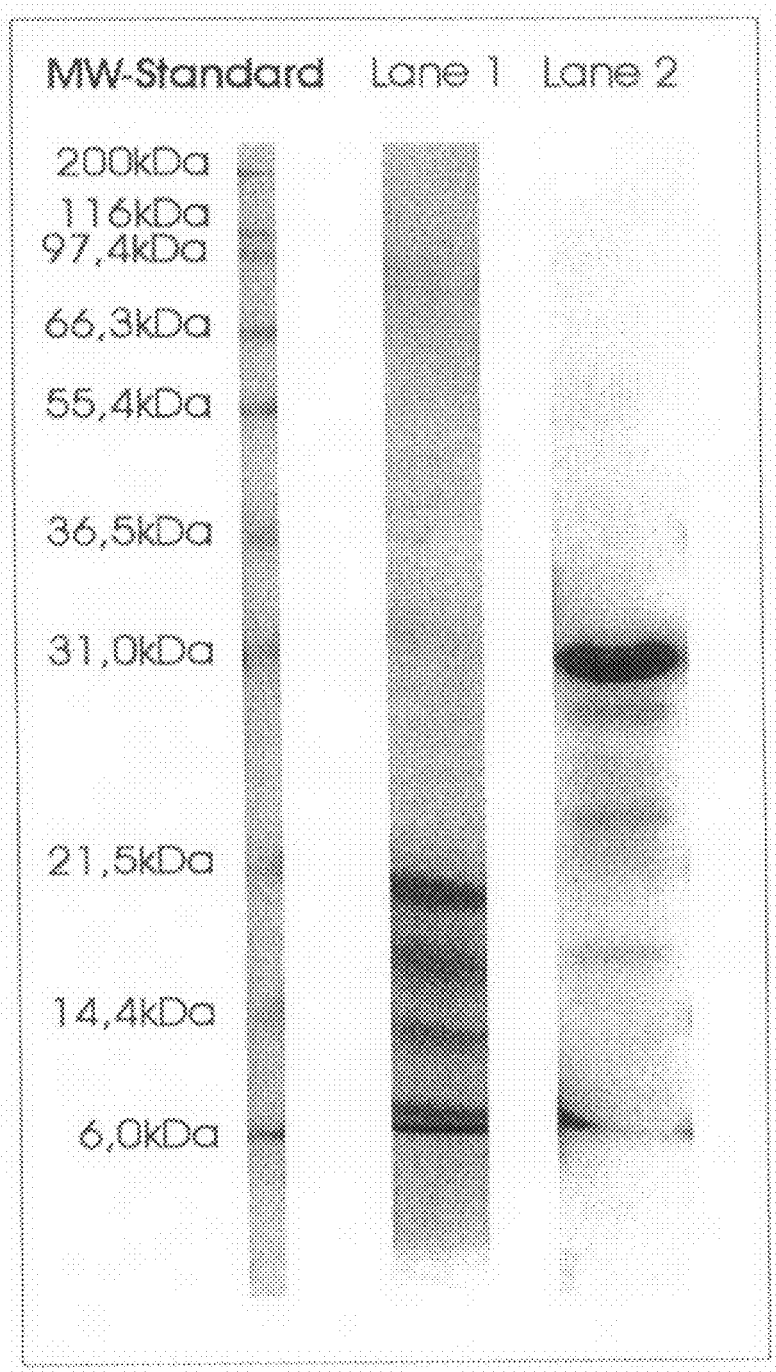
FIG. 1 shows the SDS-PAGE of ion exchange chromatography with lane 1: Eluate from ion exchange chromatograph according to Example 1A and lane 2: purified SGT after elution with 1 M arginine from affinity chromatograph according to Example 1B.

An object of the invention is to provide a simple method for the large scale purification of *Streptomyces griseus* trypsin (SGT). The methods of the invention are useful for the large scale purification of SGT, and in some embodiments which utilize a physiologically acceptable eluting agent, provide a stable SGT preparation ready-to-use for various biotechnological processes.

In one embodiment, the present invention is directed to a method of isolating SGT by a single chromatography step by contacting the PRONASE protease mixture to an immobilized affinity moiety (e.g., an amidine, a guanidine, or an amine containing species) and eluting the trypsin selectively from the column with a member of the same classes of compounds used as the affinity moiety. The eluting agent acts as a competitor to the affinity moiety that is immobilized to the carrier for the SGT. Thus, in some embodiments, the eluting agent is selected to have greater affinity for the SGT than the affinity moiety.

According to some embodiments of the invention the PRONASE protease mixture is contacted with an immobilized affinity column, which includes an amidine. As used herein, the term "amidine" includes amidine and derivatives thereof (e.g., in which the hydrogen atom attached to the amidino nitrogen (=NH) is replaced by substituted or unsubstituted alkyl groups, substituted or unsubstituted heteroalkyl groups, substituted or unsubstituted aryl groups, and substituted or unsubstituted heteroaryl groups). In these embodiments, the amidine has the structure:

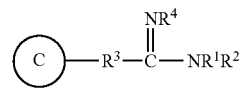

in which the circle with the inset "C" represents a component of the column or other solid support. The symbols $R^1$, $R^2$, and $R^4$ are each members independently selected from H, substituted or unsubstituted alkyl, substituted or unsubstituted heteroalkyl, substituted or unsubstituted aryl, and substituted or unsubstituted heteroaryl groups. $R^3$ can be either present or absent and can have any of the identities set forth above, with the exception of H. Representative amidine derivatives include substituted or unsubstituted benzamidine species. Amidines that can be used include, but are not limited to, benzamidine hydrochloride; p-amino-benzamidine dihydrochloride; bis(5-amidino-2-benzimidazolyl)methane; a,a'-bis(4-amidino-2-iodophenyl)-p-xylene; 1,2-bis(5-amidino-2-benzofuranyl)ethane; and 6-amidino-2-(4-amidinophenyl)benzo-[β]thiophene.

In other exemplary embodiments, the affinity moiety is a guanidine. As used herein, the term "guanidine" includes guanidine and derivatives thereof (e.g., in which the hydrogen atom attached to the amidino nitrogen (=NH) is replaced by substituted or unsubstituted alkyl groups, substituted or unsubstituted heteroalkyl groups, substituted or unsubstituted aryl groups, and substituted or unsubstituted heteroaryl groups). In these embodiments, the guanidine derivative has the structure:

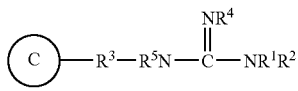

in which the circle with the inset "C" represents a component of the column or other solid support. The symbols $R^1$, $R^2$, $R^4$, and $R^5$ each represent members independently selected from H, substituted or unsubstituted alkyl, substituted or unsubstituted heteroalkyl, substituted or unsubstituted aryl, and substituted or unsubstituted heteroaryl groups. $R^3$ is either present or absent and can have any of the identities set forth above, with the exception of H. Representative guanidine-containing species include guanidinoacetic acid and derivatives thereof, substituted or unsubstituted guanidinobenzoic acid, arginine and analogues thereof (e.g., derivatized at the carboxy or α-amino group).

In yet other exemplary embodiments, the affinity moiety is an amine-containing species. Exemplary amine-containing species of use in practicing the present invention include amino acids and amino acid analogues (e.g., derivatized at the carboxy or ε-amino group). Representative amino acids of use in the invention is lysine, a derivative thereof, E-amino caproic acid, and the like.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons).

"Alkyl," as used herein also encompasses "alkylene" groups. The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Substituents for each of the above noted aryl and heteroaryl ring systems are selected from the group of acceptable substituents described below.

As noted above, the eluting agent is the same as, or is an analogue of, the affinity moiety used. Typically, the eluting agent will have greater affinity for the SGT than the affinity moiety on the column. In some embodiments, the eluting agent is arginine. The concentration of the eluting agent (e.g., arginine) in the eluant is usually at least about 0.5 M. It has been found that concentrations between about 0.5 M and about 1.2 M in the eluant provides a preparation of SGT having a high purity. Most preferred is a concentration between about 0.8 M and about 1.0 M. The yield obtained by the methods of the invention is higher compared to prior art ion exchange chromatography methods.

In the method provided, SGT is selectively purified from a mixture of various proteases, some of them, particularly chymotrypsin, have similar physiochemical characteristics which are difficult to separate with known methods. However, with the method of the invention using arginine in a concentration between about 0.5 M and about 1.2 M in the eluant, SGT is selectively separated from other proteases in the PRONASE protease mixture.

The eluant typically comprises arginine as the eluting agent and can have a pH between about pH 4.0. and about 9.0., preferably between about pH 5.0 and about 7.0. Other amidine derivative analogues that can be used include, but are not limited to analogues of arginine such as those with modification on the carboxyl-end of the molecule (see, e.g., Kasai, K. (1992) *J. Chromatography* 597:3-18); peptides, containing arginine as the C-terminal amino acid such as leupeptin, pepstatin (see, e.g., Kasai, supra); lysine or analogues of lysine and peptides containing lysine as C-terminal amino acid; sulphamethoxazolum and derivatives thereof (see, e.g., Wu, X. and Liu, G. (1996) *Biomedical Chromatography* 10:228-232); benzamidine and its analogues with modifications at the m- and/or p-positions; and guanidine and derivatives thereof (see, e.g., Ellouali, et al. (1991) *J. Chromatography* 548:25-265).

The eluant can further comprise an inorganic salt. The inorganic salt can be a salt from sodium, phosphate or sulfate. Generally, a sodium salt, such as NaCl is preferred. The inorganic salt can be in a concentration between about 0.1 M and about 1 M. A concentration of between about 0.5M and about 1.0 M in the eluting agent is preferred.

The method of the invention is conveniently carried out on an affinity chromatography column. Any matrix to which the affinity moiety can be bound can be used for the affinity carrier. Such matrix or carrier can be selected from agarose, such as Sepharose® (Pharmacia), porous particles or beads, such as Poros® (Applied Biosystems), or Toyopearl® (Tosohaas) or other carriers based on cellulose, dextrane, acrylate or silicate.

In the methods of the invention, the PRONASE protease mixture is preferably solubilized. The solubilizing agent can be a buffer, wherein the buffer solution can be a Tris-HCl buffer, phosphate buffer, or sulfate buffer. Optionally, the buffer can comprise a salt, such as sodium salts. The buffer preferably has a pH between about 6.0 and about 8.0. The PRONASE protease mixture is contacted with the carrier matrix and SGT is selectively eluted by competitive elution, typically with arginine.

When utilizing arginine as the eluting agent, the purified SGT obtained by this method is in a solution comprising about 0.5M to about 1.2M arginine. An advantage of this embodiment is that no stabilization agent has to be added because of the stabilizing properties of the eluting agent (e.g., arginine) in the solution. Therefore, the purified SGT can be stored without any further stabilizer in liquid. The SGT obtained by the method has a purity of at least about 95%, preferably at least about 98% and is essentially free of any other enzymes, such as e.g. chymotrypsin.

In some embodiments when the eluting agent is not physiologically acceptable, the eluting agent is removed from the purified SGT. Any of a number of standard methods are used for this purpose. Such methods include dialysis or ultrafiltration using membranes with appropriate molecular weight cut off, allowing the eluting agents to pass through, while the SGT is retarded in the retentate. Such membranes are well known and can be manufactured from regenerated cellulose, PVDF, polyethersulfones and the like. Various chromatography techniques, making use of molecular differences such as size, charge, hydrophobicity, affinity and the like are also conveniently used. Other methods involve precipitation of either the eluting agent or the SGT and rely on the different solubility properties of the eluting agent compared to SGT. Generally, when high affinity eluting agents are used, the eluting agent must first be separated from the SGT before the agent can be removed. This is typically done by changing environmental parameters such as pH, ionic strength, temperature, dielectric constant, and the like. Such methods are also well known in the art.

The invention further provides preparations of purified SGT having a purity of at least about 95%. Often, the purified preparation comprises arginine in a concentration of at least about 0.6 M arginine. The SGT preparation of the present invention has a specific activity of at least about $25 \times 10^3$ U/mg protein. Preferably, the specific activity is at least about $40 \times 10^3$ U/mg protein.

A preparation of the invention is typically stable at room temperature in a solution of between about 0.5M to about 1.2M arginine for at least 2 weeks and at 4° C. for at least 4 weeks. For longer storage the preparation can be kept frozen or can be lyophilized.

As used herein, "stable" means that the decrease of specific activity of the original preparation of SGT obtained directly by elution from affinity carrier is less than 5% at room temperature per 24 h.

"Purified preparation of SGT" means a preparation having a purity of at least about 95% as determined by western blot analysis and HPLC. The purity of SGT can also be determined by residual chymotrypsin activity of the preparation. Possible residual chymotrypsin activity in the preparation is determined by chymotrypsin specific enzyme test. These assays can be carried out, for example, as described in Example 1. If the test results show no detectable chymotrypsin activity in the preparation, the preparation is defined as free of chymotrypsin activity.

"Specific activity" can be determined by a number of methods. One example is a specific trypsin activity test, such as esterase activity with a specific substrate, such as N-benzoyl-L-arginine ethyl ester (BAEE) or N-benzoyl-L-isoleucyl-L-glutamyl-glycyl-L-arginine-p-nitroanili-de hydrochloride (S222). These assays are carried out, for example, as described in Examples 1 and 2.

"Specificity" means the specific inhibition of the purified SGT by a trypsin-specific inhibitor. The trypsin-inhibitor can be from a plant or an animal source, such as trypsin-inhibitor from soybeans or chicken egg white.

As a control for all enzymatic assays purified commercial available trypsin from a porcine or bovine source can be used.

When using a physiologically acceptable eluant such as arginine, the methods of the present invention are efficient and simple because only a single chromatographic step is needed to obtain a highly purified preparation of SGT. The preparation is stable in the eluting agent and can be stored in the solution without significant loss of enzymatic activity. With this method purified SGT with a good yield, high specific activity and purity is obtained.

The invention provides for a method of purifying SGT by adsorbing the enzyme selectively to an affinity moiety (e.g., benzamidine) and eluting intact SGT by competitive elution with an analogue of the affinity moiety (e.g., arginine). By using the very gentle method of competitive elution, the bleeding of the ligand, such as benzamidine, into the final product is avoided. Furthermore, the large excess of the eluting agent, e.g., arginine, inhibits the autocatalytic activity of the enzyme by avoiding autodigestion during preparation and storage and maintains a stable purified product. Another advantage is that the final product can be directly used for its intended purposes in a biotechnology process, since arginine is fully compatible with most cell culture or purification processes.

The physiological characteristics of the final purification product made according to the invention allow its direct use in e.g. cell culture techniques, protein purification process or any other process where trypsin is used. Because of the very similar mode of action and specificity, SGT can be used as a replacement for mammalian trypsin in virtually all biotechnological applications. When purified to a high degree of uniformity, the enzyme can be inhibited completely by the well known trypsin inhibitors.

According to another aspect of the invention, the purified SGT of the invention is used in a biological process, such as cell culturing, virus activation or purification. For example, the purified SGT is used for detachment of eukaryotic cells from a matrix, and optionally further subculture of the cells, or for inoculation in a fermenter. The SGT of the invention can be used for propagation of cells and/or production of a cell culture biomass of vertebrate cells.

The SGT of the invention can also be used for production of a cell biomass or for passaging of surface dependent eukaryotic cells on culture plates, Roux flasks, roller bottles or microcarrier culture. The culture can be a monolayer culture, a microcarrier culture, for suspension of cells from a layer, isolation and separation of cells from tissue or preparation of primary cell culture. The vertebrate cell can be any cell derived from a tissue of an animal, such as an organ, from primary cells or cells from a continuous cell line. Primary cells can be from monkey kidneys, hamster kidneys, dog kidneys, ovarian or other organs known to be useful for production of primary cell cultures. Examples of cells from a continuous cell line are VERO; CV-1, CHO; BHK; MDCK; MRC-5, MDBK, WI-38, and include transformed, transfected and recombinant cells.

The cells are preferably cultivated and grown in serum free medium. The medium can be a minimal medium, such as DMEM or DMEM HAM's F12 and other minimal media known in the art, such as described in Kistner et al. (1998) *Vaccine* 16:960-968. Most preferably, the cells are grown in a serum and protein free medium as described in WO 96/15213, WO 00/0300 or WO 01/23527, whereby said minimal medium can be supplemented with extracts of yeast or soy peptone.

According to another aspect of the invention the purified SGT is used for production of virus or virus antigen. The methods comprise the steps of providing a cell culture, by passaging and subculturing the cells using purified SGT of the invention, growing the cells to a biomass and infecting the cells with a virus. The cells are preferably cultivated and grown in serum free or serum and protein free medium.

The methods provided by the invention combines a cellular biomass and virus production process, wherein all steps are performed under conditions avoiding any mammal derived source, such as serum or protein in the medium. Furthermore, during passaging and subculture the protein load can be reduced due to the high specific activity of the SGT in the cell culture. The method therefore reduces the overall protein load of contaminating protein significantly.

Examples of viruses that can be used for the invention are those of the group of virus families of orthomyxoviridae, paramyxoviridae, reoviridae, picornaviridae, flaviviridae, arenaviridae, herpesviridae, poxyiridae, rhinoviridae and reoviridae and adenoviridae, preferably those selected from the group of Poliovirus, Influenza virus, Ross River Virus, Hepatitis A Virus, Rubella virus, Rota Virus, Mumps virus, Measles Virus, Respiratory Syncytical Virus, Vaccinia Virus and recombinant Vaccinia Virus, Herpes Simplex Virus, TBEV, Japanese encephalitis Virus, West Nile Virus, Yellow Fever Virus and chimerics thereof. Methods for selecting an appropriate host cell and a virus susceptible to the host for propagation of the desired virus are well known. Cells can be selected from the cells as described above.

According to a particular embodiment, the purified SGT is used for production of virus or virus antigen, wherein the virus is activated by a protease. Such viruses are those selected from the group of paramyxoviridae, orthomyxoviridae, rotaviridae. The methods comprise the steps of providing a cell culture, wherein the cells have been passaged and subcultured using purified SGT of the invention, infecting the cells with virus selected from the group of paramyxoviridae, orthomyxoviridae, rotaviridae, contacting the virus with purified SGT to activate the virus, propagating the virus and harvesting virus produced.

For passaging and subculture of the cells, purified SGT of the invention is added in an amount of between about 4 μg and about 1000 μg, depending on the cell culture type, the culture or medium volume, and the specific activity of the purified SGT used in the culture process. The amount of protein added for a static culture can be in the range of about 4 μg/150 $cm^2$ to about 50 μg/150 $cm^2$, for a roller bottle in the range of about 50 μg/850 $cm^2$ to about 100 μg/850 $cm^2$, and for a microcarrier culture in the range of about 1000 μg to about 2000 μg/liter of medium with an SGT preparation having a specific activity of about $26\times10^3$ U/mg protein. It is within the knowledge of a skilled artisan to determine the minimal amount of protease/protein needed for optimal passaging and subculture conditions. The advantage of use of purified SGT of the invention is (i) to avoid protein from an animal source, and (ii) to reduce protein load due to the high specific activity of the SGT between at least 5 fold to at least 25 fold compared to a conventional cell culture, wherein trypsin from an animal source is used.

According to one aspect of the invention the purified SGT of the invention is used for production of a cell biomass grown in serum and protein free medium, wherein said biomass is passaged and subcultured using purified SGT and the total protease protein load is reduced at least by 75% compared to a cell culture cultivated under identical conditions by use of mammalian-derived trypsin.

For activation of the virus, purified SGT of the invention can be used in a total protein amount of about 10 μg to about 500 μg of culture volume ($cm^2$ or $cm^3$), depending of the specific activity of the purified SGT used. It is within the knowledge of a person skilled in the art to follow the examples as described and adapt total protein amount needed of purified SGT having a particular specific activity of at least of $2\times10^4$ U/mg for optimal virus activation and further virus propagation.

By using purified SGT preparation for passaging subculture and optionally virus activation, the protein load derived from biomass production and virus propagation process can be reduced at least by 75%, preferably at least 90% compared to a cell culture obtained by conventional methods.

By the method described a virus or virus antigen preparation is obtained, wherein the total protein load of contaminating protein derived from the cells and the cell culture medium is reduced by at least 75% compared to a preparation obtained by a conventional cell culture, that has been cultivated under similar conditions but using mammalian derived trypsin.

The method as described above using purified SGT of the invention to culture cells and optionally activate virus can further comprise the step of purifying the virus produced. Due to the low load of contaminating protein (protein which is not product/virus specific) residual contaminating protein can be removed by further purification. The purified virus preparation obtained can be further formulated in an immunogenic composition such as a prophylactic or therapeutic vaccine.

According to another aspect of the invention the purified SGT is used in a purification process. For a wide range of purification methods specific proteases, such as trypsin are used to degrade contaminating proteins, which are then removed by further purification steps, such as filtration, chromatography or centrifugation. The purified SGT of the invention can be used efficiently in a purification method for preparation of purified virus, such as HAV. It is within the knowledge of a skilled person in the art to determine the minimal purified SGT of the invention needed for optimal conditions.

The purified SGT of the invention can also be used for the production of recombinant products from recombinant cells. This use comprises the steps of providing a cell culture of recombinant cells expressing a foreign polypeptide or protein, wherein said cells are passaged and subcultured using purified SGT of the invention, culturing the cells under conditions, whereby recombinant polypeptide or protein is produced and harvesting said recombinant polypeptide or protein produced. The cells are preferably grown in serum or serum and protein free medium. The cells can be recombinant cells, such as recombinant CHO cells, being able to express a recombinant protein.

By the method described a recombinant product is obtained, wherein total protein load of contaminating protein derived from the cells and the cell culture medium is reduced by at least 75% compared to preparation obtained by a conventional cell culture, that has been cultivated under similar conditions.

According to another aspect purified SGT of the invention is used for controlled processing of pro-proteins to their mature form, either in liquid or immobilized on an insoluble carrier as described, for example, in U.S. Pat. No. 6,010,844.

The purified SGT of the invention can be used for cleaning of biotechnological equipment, such as filters, fermenters etc. which are contaminated by proteins, which can be digested by proteolytic activity of SGT.

Having now generally described this invention, the invention can be understood by reference to the following examples which are provided herein for purposes of illustration only and are not intended to be limiting.

EXAMPLE 1

Purification of *Streptomyces Griseus* Trypsin from Pronase Protease Mixture.

A. Ion Exchange Chromatography 30 g of PRONASE protease mixture (Boehringer Ingelheim) is dissolved in Buffer A (0.02 pyridin, pH 5.0) to a final concentration of 40 mg/ml PRONASE protease mixture. 25 ml of the solution is subjected to cation exchange chromatography on CM Sepharose Cl 6B (Pharmacia) equilibrated with buffer A. The elution is performed at room temperature using a linear gradient with buffer A (0.02 M pyridin) and buffer B (0.02 pyridin pH 5.0) with 5 times the column volume.

Collected fractions are tested for inhibiting properties by mixing samples of the fractions with soy bean inhibitor in a 1:10 ratio (e.g. 1 mg soy bean inhibitor/100 µg protein) followed by a chromatographic substrate assay using S2222. The results are expressed as A absorbance units per minute (Δ A/min). The fraction having the highest inhibiting activity to soy bean inhibitor is further analyzed by SDS-PAGE and stained with Coomassie (FIG. 1, lane 1).

The trypsin activity is measured by chromogenic assay using N-benzoyl-L-arginine ethyl ester (BAEE, in Tris buffer pH 8.0, 20 mM $CaCl_2$, 25° C.) as substrate and A absorbance units per minute is determined. As a control reference, porcine trypsin solution (1 mg/ml) with a specific activity of $13 \times 10^3$ U/mg is used. The specific activity is defined as the units of trypsin enzyme activity per mg protein. The results are summarized in Table 1.

The chymotrypsin activity is measured by chromogenic assay using 3-carboxymethoxypropionyl-L-arginyl-L-propyl-L-tyrosine-p-notroaniline hydrochloride (S-2586, Chromogenix). The results are expressed as Δ A absorbance units per minute (Δ A/min).

TABLE 1

Purification of PRONASE protease mixture by ion exchange chromatography

| *Streptomyces griseus* PRONASE protease mixture | PRONASE protease mixture unpurified | Purified fraction |
|---|---|---|
| Protein (g) | 1 | 0.08 |
| Specific activity U/mg | $1.6 \times 10^3$ | $16.5 \times 10^3$ |
| Recovery U in % | 100 | 70 |
| Stability by SDS-PAGE | n.d. | Unstable, low molecular weight fragmentation |
| Inhibition by soy bean inhibitor (% inhibition) | n.d. | 90 ± 0.1 |
| Chymotryspin activity (ΔA/min) | 450 | 38 |

* n.d. not determined

Table 1 shows that the fractions containing a protein having trypsin-like activity, as determined by inhibition test with soy bean inhibitor, can be purified by ion exchange chromatography with a specific activity which is about 10 times higher than that of PRONASE protease mixture and with a recovery of about 70%. However, the protein is unstable and shows not a single band, but various bands in SDS-PAGE. This is indicative of fragmentation and autocleavage of the protein (FIG. 1, lane 1).

B. Affinity Chromatography on Immobilized Benzamidine

A Benzamidine Sepharose 6B fast flow (Pharmacia) column equilibrated with buffer A (50 mM Tris, 0.5 M NaCl pH 7.0) is loaded with 40 ml of a PRONASE protease mixture solution (75 mg/ml, buffer A). Elution is performed with buffer B (50 mM Tris, 0.5 M NaCl pH 7.0, 10 mM benzamidine hydrochloride pH 7.0), buffer C (0.5 M NaCl, 0.6 M arginine, pH 5.5) or buffer D (0.5 M NaCl, 1 M arginine, pH 5.5).

The fractions collected are tested for inhibiting properties using soy bean inhibitor, as well as trypsin and chymotrypsin activity as described in Example 1A. The specific activity is determined as units of enzyme activity per mg protein.

TABLE 2

Purification of PRONASE protease mixture by affinity chromatography on immobilized benzamidine and elution with benzamidine
AFFINITY CHROMATOGRAPHY AND ELUTION WITH BENZAMIDINE (BUFFER B)

| *Strepromyces griseus* PRONASE protease mixture | PRONASE protease mixture unpurified | Purified fraction |
|---|---|---|
| Protein (g) | 3 | 0.13 |
| Specific activity U/mg | $1.6 \times 10^3$ | $19 \times 10^3$ |
| Recovery U in % | 100 | 60 |
| Stability by SDS-PAGE | stable | stable |
| Inhibition by soy bean inhibitor (% inhibition) | n.d. | 99.98 ± 0.1% |
| Chymotryspin activity (ΔA/min) | n.d. | 0.1 |

The results summarized in Table 2 show that by competitive elution with benzamidine, 60% of purified trypsin-like activity of PRONASE protease mixture is recovered with a high specific activity. However, the purified trypsin-like protease containing fraction is preferably further purified and the benzaminide removed prior to use in processes which involve cell culture growth or production of biologicals for application in humans.

TABLE 3

Purification of PRONASE protease mixture by affinity chromatography on immobilized benzamidine and elution with 0.6M arginine and 1M arginine

| *Streptomyces griseus* PRONASE protease mixture | PRONASE protease mixture unpurified | Purified fraction |
|---|---|---|
| AFFINITY CHROMATOGRAPHY AND ELUTION WITH 0.6 M ARGININE (BUFFER C) | | |
| Protein (g) | 3 | 0.13 |
| Specific activity U/mg | $1.6 \times 10^3$ | $26 \times 10^3$ |
| Recovery U in % | n.d. | 63 |
| Stability by SDS-PAGE | stable | stable |
| Inhibition by soy bean inhibitor (% inhibition) | n.d. | 99.89 ± 0.1% |
| Chymotrypsin activity (ΔA/min) | n.d. | <0.1 |
| AFFINITY CHROMATOGRAPHY AND ELUTION WITH 1M ARGININE (BUFFER D) | | |
| Protein (g) | 3 | 0.13 |
| Specific activity U/mg | $1.6 \times 10^3$ | $46.5 \times 10^3$ |
| Recovery U in % | n.d. | 71% |
| Stability by SDS-PAGE | stable | stable |
| Inhibition by soy bean inhibitor (% inhibition) | n.d. | 99.99 ± 0.1% |
| Chymotrypsin activity (ΔA/min) | n.d. | <0.1 |
| LAL (EU/1000U) | 88 | <4 |

As can be seen from results in Table 3, about 63% of the initial trypsin-like activity of PRONASE protease mixture is recovered when using a buffer comprising 0.6 M arginine, whereas about 71% is recovered with a buffer comprising 1M arginine. The purified SGT eluted with arginine from a benzamidine affinity carrier also has a higher specific activity compared to SGT obtained by ion exchange chromatography or elution with benzamidine from a benzamidine carrier. Further, a product of higher purity and specific activity is obtained when a buffer comprising increasing molarity of arginine is used.

Figure 2:
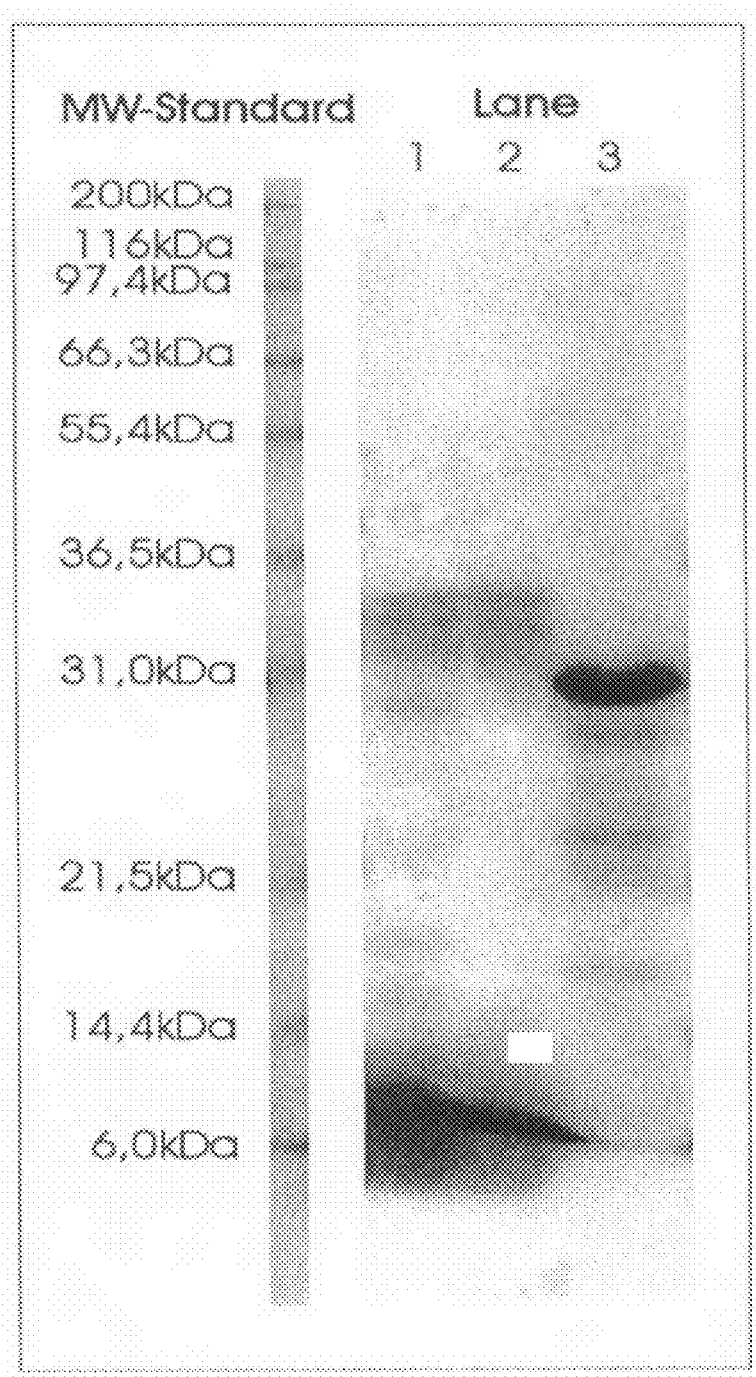
FIG. 2 shows the SDS-PAGE of unpurified *Streptomyces griseus* PRONASE protease mixture and purified SGT, with lane 1: unpurified PRONASE protease mixture, lane 2: flow through of the affinity chromatography and lane 3: purified *Streptomyces griseus* trypsin after affinity chromatography and elution with 1 M arginine.

Samples of the unpurified *S. griseus* PRONASE protease mixture, the flow through of the affinity chromatography column and the purified SGT of the elution with 1M arginine are analysed by SDS-PAGE (FIG. 2)

Figure 3:
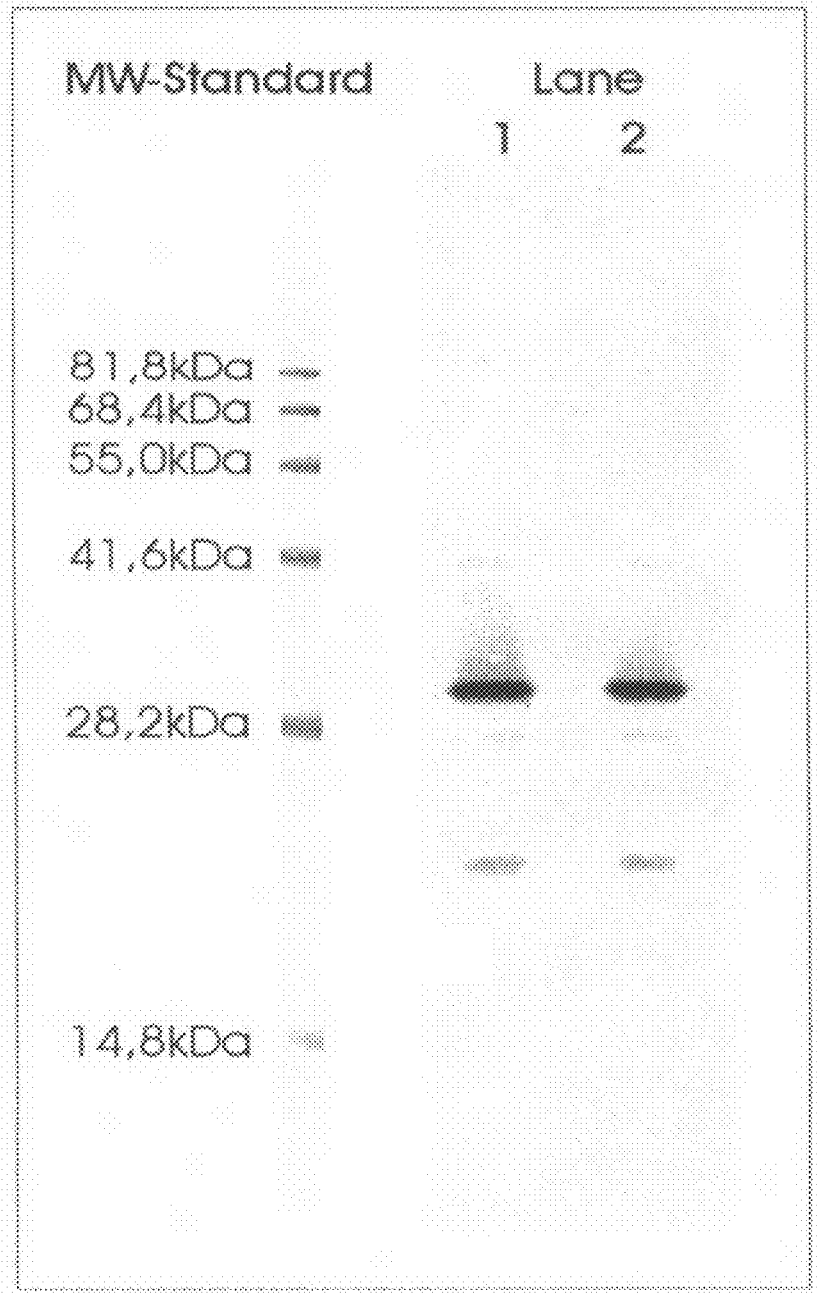
FIG. 3 shows western blot analysis of two different lots of purified SGT after affinity chromatography and elution with 1 M arginine.
Figure 4:
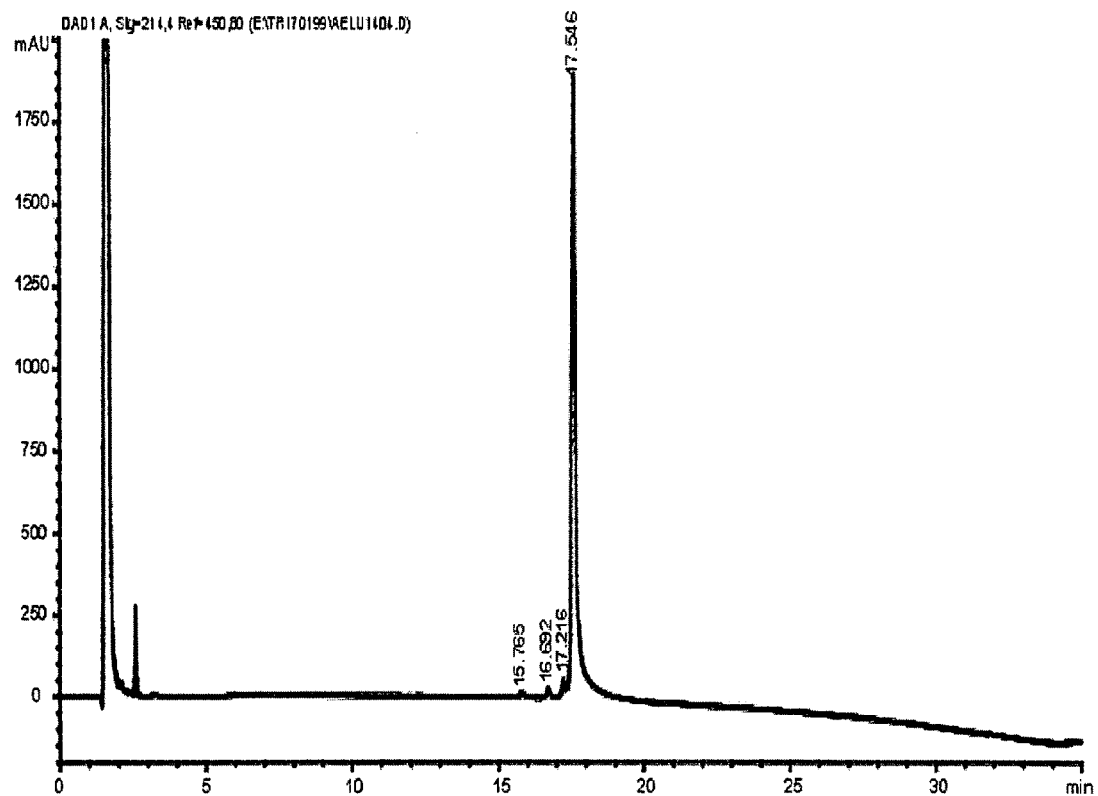
FIG. 4 shows the chromatogram of the reversed Phase HPLC of the purified SGT.

Samples of the fractions having the highest inhibiting activity to soy bean inhibitor are further analyzed by western blot with anti-SGT serum derived from guinea pigs (FIG. 3). The purity of the SGT is determined by analytical Reversed Phase HPLC, wherein purified SGT is loaded onto a reverse phase column (Nucleosil 300-5C18-150×2 mm) and eluted with a linear gradient of acetonitril. The chromatogram of the reversed HPLC is given in FIG. 4. Purity is expressed as the relation of the main peak to the total peak area. The Reversed Phase HPLC of purified SGT demonstrated a purity of >95%. The chromatogram shows a sharp peak which corresponds to SGT. Online HPLC-electroscopy ionization mass spectroscopy (ESI-MS) is used to determine the molecular weight of purified SGT. As such, the major peak of the chromatogram has a molecular weight of 23096.5 D, which is in excellent agreement with the theoretical mass of 23099 D. The data is further corroborated by the assessment of the correct N-terminus (NH$_2$—V—V-G-G-T-R-A-A-Q-G-E-F—P—F-M-V—) SEQ ID NO:1.

The purified trypsin-like protease purified by single step affinity chromatography on benzamidine and eluted with arginine is stable in the arginine solution. The purified product shows a single band in SDS-PAGE and has no significant fragmentation to low molecular weight polypeptides as can be seen in FIG. 1 (lane 2), whereas SGT purified by ion exchange chromatography is fragmented into low molecular weight polypeptide as seen in FIG. 1 (lane 1).

The affinity chromatography purification method by competitive elution with arginine results in a purified SGT having a purity of at least 95%, which is intact and stable, as shown by SDS/western blot and HPLC. In addition, it is substantially free of other protease activities, particular chymotrypsin, endotoxins and processes related impurities, such as benzamidine. Due to the high concentration of arginine in the purified SGT preparation, the SGT is stable at room temperature for at least 2 weeks and shows no autocatalytic activity, instability of the product, increase of SGT degradation products or loss of specific activity. The stabilized SGT preparation in arginine solution of between 0.5 M to 1.2 M (pH between 2 and 10) is physiologically acceptable in most biological processes and is ready-to-use for further processes, such as activation of proteins, viruses or in purification methods as described below.

EXAMPLE 2

Determination of Enzyme Activity of Porcine Trypsin and Purified SGT Used for Cell Culturing of Mammalian Cells The protein content and the esterase activity of each enzyme is measured by the use of BAEE (N-benzoyl-L-arginine ethyl ester) as a substrate of porcine trypsin (purity grade, type IX, crystallized, Sigma), PRONASE protease mixture (purity grade, Boehringer Ingelheim) and purified SGT obtained by affinity chromatography on benzamidine Sepharose 6B and elution with 0.6 M arginine according to Example 1B. The results of this and further experiments are summarized in Table 4.

TABLE 4

Specific activity of proteases used for Vero culture experiments

| Protease | BAEE activity (Units/ml) | Protein (µg/ml) | BAEE activity/Protein (U/µg) |
|---|---|---|---|
| Porcine Trypsin | 12,555 | 940 | 13.4 |
| Crude PRONASE protease mixture | 1,844 | 740 | 1.5 |
| Purified SGT | 8,564 | 330 | 26.0 |

EXAMPLE 3

Determination of Total Protein Load for Subculture of Serum and Protein-Free VERO Cells VERO cells (African Green Monkey, Cercopthecus aethiops, kidney) obtained from the American Type Cell Culture Collection, Rockville, Md. at a passage number 124 under the designation ATCC CCL 81 are cultivated in serum and protein-free medium. Cells are adapted to grow in serum or serum and protein free medium as described in Kistner et al. (1998) *Vaccine* 16:960-968, WO 96/15231, or U.S. Pat. No. 6,100,061. For growth in serum free medium, a basal DMEM HAM's F12 medium supplemented with inorganic salts, amino acids, sodium bicarbonate (2 g/l) and yeast or soy bean extract (0.1 to 10 g/l) is used. The working cell bank is prepared without the use of any animal derived medium components. One ampoule of a working cells bank (WCB) of VERO cells cultivated in DMEM medium mixed with Ham's F12 nutrient mixture in a ratio 1:1 is resuspended in serum free medium supplemented either with soy bean or yeast extract.

Different protein concentrations between 1 µg and 10,000 µg of porcine trypsin (purity grade, type IX, crystallized, Sigma), PRONASE protease mixture (purity grade, Boehringer Ingelheim) and purified SGT having a specific activity as determined in Example 2 are added to static cultures of T-flasks, cells in roller bottles or cells bound to microcarriers. The total protein amount of trypsin, PRONASE protease mixture and purified SGT needed for complete cell detachment and subsequent attachment (subculturing) cultures is given in Table 5.

Table 5 shows that when using purified SGT, the total protein load of protease for cell detachment and passaging in a static culture is reduced to 4%, in roller bottles to 17% and in the microcarrier culture system to 20% compared to the amount needed when using trypsin.

TABLE 5

Comparison of total protein amount of protease needed for complete cell detachment and subculture of VERO cells

| Cell Culture Type | Porcine Trypsin (µg) | Purified SGT (µg) | Reduction of Protein Load |
|---|---|---|---|
| Static Culture (150 cm$^2$) | 100 | 4 | 25X |
| Roller Bottle (850 cm$^2$) | 300 | 51 | 6X |
| Microcarrier Culture (1 liter) | 5,000 | 1,000 | 5X |

EXAMPLE 4

Comparison of Mammalian-Derived Trypsin, PRONASE Protease Mixture and Purified SGT on Cell Growth On a small scale basis, cell attachment and proliferation characteristics of Vero cells grown in static cultures (T-flasks) and microcarrier cultures (Cytodex3®, Pharmacia) are compared. VERO cells are cultivated as described above in serum and protein free medium.

VERO cells are either grown in T-flasks or on microcarriers (37° C., $CO_2$ concentration 5-10%.). Subculture is performed as determined in Example 3 by using porcine trypsin (purity grade, type IX, crystallized, Sigma) and PRONASE protease mixture (purity grade, Boehringer Ingelheim) in T-flasks in a final amount of 100 µg and in microcarrier culture of 5000 µg. Purified SGT with a specific activity of $2.6 \times 10^4$ U/mg is added to T-flask culture in final amount of 4 µg and in microcarrier culture of 100 µg. Cell attachment and cell growth are measured by visual inspection and counting of non-attached cells and are expressed as proliferation activity. Table 6 shows proliferation activity expressed in % of total amount of VERO cells either grown in T-flasks or on microcarriers.

TABLE 6

Effect of Trypsin, PRONASE protease mixture, and SGT on proliferation activity of cells

| Cell culture type | Protease (µg) | | |
|---|---|---|---|
| T-flask | Trypsin<br>100 µg | PRONASE<br>protease<br>mixture<br>100 µg | Purified SGT<br>4 µg |
| Attachment/Growth | 90-100% | 90-95% | 90-100% |
| Microcarrier Culture | Trypsin<br>5000 µg | PRONASE<br>protease<br>mixture<br>5000 µg | Purified SGT<br>1000 µg |
| Attachment Growth | 95-100% | 70% | 95-100% |

As shown in Table 6, crude PRONASE protease mixture did not allow sufficient repeated transfer of Vero cells grown in serum-free medium, whereas purified SGT is as effective as porcine trypsin, but with a significantly reduced final protein load.

EXAMPLE 5

Virus Antigen Production in Vero Cells Using Purified SGT 5.1 In Vivo Activation of Influenza Virus and Virus Production in Roller Bottles Two Vero cultures are grown in roller bottles to confluency with a final cell density of about $2 \times 10^8$ per unit. The cultures are infected with Influenza virus strain Nanchang $A/H_3N_2$ with a m.o.i. of 0.01. Porcine Trypsin (total protein amount: 500 µg) or purified SGT (total protein amount: 50 µg) are added for in vivo activation of Influenza virus which allows further virus propagation. After 48 hours the hemagglutination activity in the culture is determined.

TABLE 7

In vivo activation of Influenza virus with Trypsin or purified SGT

| | Trypsin | Purified SGT |
|---|---|---|
| Amount of enzyme | 500 µg | 50 µg |
| HAU/ml after 48 hrs | 2560 | 2560 |

The data given in Table 7 show that for efficient in vivo activation of Influenza virus and virus propagation about 1/10 of the total protein amount of purified SGT is needed compared to mammalian-derived trypsin. Therefore, the use of purified SGT allowed a 90% reduction in total protein load during the in vivo activation step and yielded similar Influenza virus propagation in Vero cells as compared to mammalian-derived trypsin.

5.2 Large Scale Production of Influenza Virus Antigen on Cells Grown on Serum and Protein-Free Medium and Use Purified SGT for Virus Activation One ampoule of a working cells bank (WCB) of VERO cells cultivated in DMEM medium mixed with Ham's F12 nutrient mixture in a ratio 1:1 is resuspended in serum free medium supplemented either with soy bean or yeast extract. Vero cells with a defined passage number are thawed from liquid nitrogen and passaged in roux and roller bottles to produce sufficient cells to inoculate a 1.5 liter bioreactor. The cells are grown at 37° C. for 6-8 days. The culture conditions of oxygen saturation 20%±10% and pH 7.1±0.2 and stirring speed of 30-60 rpm are controlled. After reaching the final cell density of 1.5 $(1.0-2.0) \times 10^6$ cells/ml, the cells are detached by purified SGT (1 mg/liter) and transferred to a 10 liter bioreactor with a microcarrier concentration of 2.5 g/l (Cytodex III®, Pharmacia). The cell number is determined by trypsinization of the cells and counted with a CASY® cell counter. The cells are cultured under confluent culture conditions to reach a biomass having a cell density of $1.0-1.5 \times 10^6$ cells/ml.

The biomass is either infected with Influenza virus strain Nanchang or strain Texas-36. During the process of virus propagation and for further lytic infection cycles of Influenza virus, the virus is activated by the addition of purified SGT in a concentration of 150 µg/liter. Table 8 summarizes Influenza virus production, as determined by HAU/ml, after 72 hours.

TABLE 8

Production of different Influenza Virus strains after activation with purified SGT

| Influenza strain | HAU/ml<br>after 72 hrs |
|---|---|
| A/Nanchang 033/95 | 10,240 |
| A/Texas-36 | 5,120 |

According to the results, as given in Table 8, Vero cells passaged and scaled up with purified SGT propagated efficiently and produced Influenza virus in large scale bioreactors.

EXAMPLE 6

Purity of Influenza Virus Antigen Obtained by Propagation on Cells Grown on Serum and Protein Free Medium and Use of SGT or Trypsin for Virus Activation Two parallel cell cultures of Vero cells are propagated to a biomass as described in Example 5.2, whereby one is passaged and subcultured with Trypsin and one with purified SGT in roux and roller bottles to produce sufficient cells to inoculate a 1.5 liter bioreactor. After reaching the final cell density of 1.5 (1.0-2.0)×10$^6$ cells/ml, the cells are detached by purified SGT or Trypsin and transferred to a 10 liter bioreactor with a microcarrier concentration of 2.5 g/l. After reaching confluent culture conditions by reaching a cell density of 1.0-1.5×10$^6$/ml the biomass is infected with Influenza virus strain Texas-36 (m.o.i. 0.01). For virus activation purified SGT or Trypsin is added to the respective cell culture. At the end of the virus propagation process the clarified supernatant harvest containing the virus is purified by ultracentrifugation on a sucrose gradient. The purity of the sucrose gradient purified antigen is determined by the antigen to protein ratio. The concentration of hemagglutinin is determined by single radial immunodiffusion (SRD), as described by Wood et al. (1977) *J. Biol. Stand.* 5:237-247, and the results are compared after 72 hrs for strain A/Texas-36. The results are summarized in Table 9.

TABLE 9

Comparison of purity of Influenza virus preparations propagated by use of purified SGT or Trypsin.

| Activating protease | HAU/ml after 72 hrs | SRD (µg/liter) | SRD/Protein Ratio |
|---|---|---|---|
| Purified SGT | 5,120 | 1245 | 0.32 |
| Trypsin (porcine) | 10,240 | 1125 | 0.13 |

The Influenza virus preparation obtained from Vero cells passaged and scaled up with purified SGT allowed the production of virus antigen with lower protein contamination. These results show that after a simple first purification step, a higher purity virus preparation is obtained as compared to using trypsin. Furthermore, an increase in volumetric bioreactor productivity (expressed as total SRD per reactor volume) of 45% has been obtained.

EXAMPLE 7

Production of Hepatitis A Virus 7.1 Production of HAV Antigen on Cells Grown on Serum and Protein Free Medium Full length cDNA of the genome of attenuated strain HM175/7 cloned into the bacterial plasmid pHAV/7 (Cohen et al., (1987) *J. Virol.* 61:3035-3039) is used to prepare full length genomic RNA by in vitro transcription. Serum and protein free VERO cells at 34° C. are transfected with in vitro transcribed HAV RNA to generate virus stocks of HAV HM175/7 free of adventitious agents. VERO cell biomass is prepared according to Example 5.2.

For large scale production of HAV HM175/7 virus, VERO cell cultures at a biomass of 1×10$^{11}$ cells are seeded on a microcarrier and propagated at 37° C. under serum free medium conditions in a 100 liter fermenter. The temperature is lowered to 34° C. and during the subsequent fermentation cycles the cell number increases 8 to 10 fold. The cells are infected in the final fermenter with HAV at a m.o.i. of 0.01 to 0.1. Propagation of the infected cells at 34° C. up to 350 days can be performed with permanent perfusion of the cell culture medium. When virus antigen is detected in the medium, the virus containing supernatant is collected and stored at 4° C. The harvest of the cell culture supernatant is started at days 35-45 after infection.

7.2 Purification of HAV Harvest and Characterization of Purified HAV

The HAV harvest of cell culture supernatant of Example 7.1 is concentrated 100 times by ultrafiltration on a Prostak Ultrafilter 200 K followed by a diafiltration step (Prostak 200 K, Diafilter) with a buffer exchanged to 50 mM Tris buffer pH 8.0, 0.01% Tween. Residual host cell nucleic acid that may be present in the preparation is removed by incubation of the Diaretenate with Benzonase®, an endonuclease from *Serratia marcescens*, commercially available as Benzonase® (Benzon PharmaA/S) in a concentration of 1000 U/l (solved in 1 mM MgCl$_2$) for 3 hours at room temperature. Subsequently, purified *Streptomyces griseus* trypsin (SGT) at a concentration of 0.5 to 5 U/ml is added and the retentate is further incubated for 24 hours at room temperature. The host cell contaminants, i.e. nucleic acids and/or proteins, are removed by diafiltration on a 100K membrane with a 20 mM PBS pH 7.4 as buffer.

Samples containing at least 1000 ELISA units/ml of HAV antigen are taken during each filtering step, subjected to SDS-PAGE, and silver stained to visualize total protein or analyzed by western blot analysis to determine HAV specific antigens. HAV specific antigens are identified by western blot analysis using an antiserum specific for HAV capsid proteins. It could be shown that HAV precursor proteins are removed during the purification process. HAV specific polypeptides are detected in the starting material of cell culture supernatant that are not present in the diaretentate after treatment with purified SGT whereas the HAV specific capsid proteins VP1, VP2 and VP3 are not affected by protease treatment. The analysis of different intermediates by silver staining and western blot clearly demonstrates the efficacy of the protease treatment purification procedure using purified SGT.

Western blot analysis using an antiserum raised against VERO cell proteins showed that in the starting material and purification intermediates of a broad range of predominantly high molecular weight VERO proteins are detectable. However, in the final retentate only minor VERO cell protein contaminants are detectable. This shows that the treatment with the highly purified SGT efficiently degrades VERO cell protein contaminants and HAV precursor polypeptides during HAV production and purification process.

EXAMPLE 8

Activation of Prothrombin to Thrombin by Immobilized Purified SGT and Recovery of the Thrombin by Affinity Chromatography Purified SGT (100 mg protein/g wet gel) is coupled to agarose-gel (5000 BAEE U SGT/ml gel). A glass-column is filled with 0.1 ml of immobilized SGT-agarose and recombinant prothrombin is subjected to the immobilized SGT under identical conditions are described in U.S. Pat. No. 6,010,844. Thrombin is isolated and prepared according to the method describe in U.S. Pat. No. 6,010,844, which method is incorporated herein by reference.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference for all purposes.

What is claimed is:

1. A method of isolating *Streptomyces griseus* trypsin (SGT) from *Streptomyces griseus* Pronase, the method comprising contacting said Pronase with an immobilized affinity moiety selected from the group consisting of an amidine, a guanadine, or an amine containing species and eluting said SGT selectively from said immobilized affinity moiety with an eluant comprising arginine, wherein the isolated SGT further comprises arginine and has a specific activity of at least $25 \times 10^3$ U/mg protein.

2. The method of claim 1, wherein said arginine is in a concentration between 0.5-1.2 M.

3. The method according to claim 1, wherein said eluant has a pH in the range of between about pH 4.0. and about 9.0.

4. The method according to claim 1, wherein said affinity moiety is benzamidine.

5. The method according to claim 1, wherein said eluant comprises an inorganic salt in a concentration between about 0.1 and about 1 M.

6. The method according to claim 1, wherein said SGT is obtained in a solution comprising 0.5 to 1.2 M arginine and has a purity of at least 95%.

7. The method according to claim 1, further comprising removing the eluting agent from the purified SGT.

* * * * *